United States Patent [19]
Barbas, III et al.

[11] Patent Number: 5,985,626
[45] Date of Patent: Nov. 16, 1999

[54] CATALYTIC ANTIBODY/SUBSTRATE INTERMEDIATES

[75] Inventors: Carlos F. Barbas, III, San Diego; Richard A. Lerner, La Jolla, both of Calif.; Juergen Wagner, Basel, Switzerland

[73] Assignee: The Scripps Research Institute, La Jolla, Calif.

[21] Appl. No.: 09/053,818

[22] Filed: Mar. 31, 1998

Related U.S. Application Data

[63] Continuation of application No. 08/573,415, Dec. 15, 1995, Pat. No. 5,733,757, which is a continuation-in-part of application No. 08/209,525, Mar. 10, 1994, Pat. No. 5,571,681.

[51] Int. Cl.⁶ .............................. C12P 7/26; C12P 13/00
[52] U.S. Cl. ................... 435/128; 435/148; 435/188.5
[58] Field of Search ................................. 435/128, 148, 435/188.5

[56] References Cited

U.S. PATENT DOCUMENTS 5,571,681  11/1996  Janda ........................................ 435/7.6

OTHER PUBLICATIONS

Wagner, J. et al. (1995) Science 270, 1797–1800.

Lerner, R. A., et al. (1990) Acta Chem. Scand. 50, 672–678.

Reymond, J–L., et al. (1995) J. Org. Chem., 60, 6970–6979.

Teraishi. K., et al. (1994) J. Mol. Graphics 12, 282–285.

Flanagan, M. E., et al. (1996) J. Am. Chem. Soc. 6078–6079.

*Primary Examiner*—Charles L. Patterson, Jr.
*Attorney, Agent, or Firm*—Donald G. Lewis

[57] ABSTRACT

Antibodies that catalyze the aldol reaction are generated by immunization with a reactive compound that covalently traps a Lysine (Lys) residue in the binding pocket of the antibody by formation of a stable vinylogous amide, i.e., a covalent antibody/hapten complex. The resultant catalytic antibodies employ a catalytic mechanism which mimics the catalytic mechanism employed by natural class I aldolase enzymes.

7 Claims, 13 Drawing Sheets

| Reaction | $k_{cat}$ [min$^{-1}$] | $K_M$ [μM] |
|---|---|---|
| (6+7) R-CH(CH3)-CHO + acetone → R-CH(CH3)-CH(OH)-CH2-CO-CH3 (9,10) | [a]8.3 10$^{-2}$ <br> 4.0 10$^{-2}$ | [a]125 <br> 48 |
| 12 R-CH2-CHO + acetone → R-CH2-CH(OH)-CH2-CO-CH3 (13,14) | 6.7 10$^{-3}$ | 17 |
| 12 R-CH2-CHO + 2-butanone → 15 (94) + 16 (4) | 1.8 10$^{-2}$ | 52 |
| 12 R-CH2-CHO + 3-pentanone → 17 | 5.1 10$^{-3}$ | 115 |
| 12 R-CH2-CHO + 2-pentanone → 18 (73) + 19 (27) | 3.5 10$^{-3}$ | 374 |

[a)] Reaction using antibody 33F12

CATALYTIC ANTIBODY/SUBSTRATE INTERMEDIATES

CROSS-REFERENCE TO RELATED APPLICATION

This is a continuation of application Ser. No. 08/573,415, filed Dec. 15, 1995, now U.S. Pat. No. 5,733,757, which was a continuation-in-part of application Ser. No. 08/209,525, filed Mar. 10, 1994, now U.S. Pat. No. 5,571,681.

STATEMENT OF GOVERNMENT RIGHTS

This invention was made with government support under the National Cancer Institute grant No. CA 27489. The U.S. government has certain rights in the invention.

FIELD OF INVENTION

The invention relates to catalytic antibody/substrate intermediates and to adducts produced by condensing β-diketone with a catalytic antibody or with a catalytic molecule containing an antibody combining site portion.

BACKGROUND

The aldol addition reaction is a reversible reaction involving the combination of two reactant molecules and the formation of a product having a new carbon-carbon bond. Each of the reactants contains a carbonyl group, i.e., either an aldehyde or ketone. During the reaction, one of the reactants loses a proton from the carbon atom next to its carbonyl group, thereby becoming nucleophilic. The nucleophilic carbon of the first reactant then attacks the carbonyl group of the second reactant. The reverse of this condensation reaction can also occur and entails the cleavage of a carbon-carbon bond and the dissociation of a molecule into two components. The aldol addition reaction is important in the glycolytic pathway and is catalyzed by aldolase enzymes. The aldol addition reaction is also fundamental to organic chemistry for the formation and dissociation of carbon-carbon bonds. In organic chemistry, the reaction may be catalyzed by base.

Two mechanistic classes of aldolase enzymes have evolved, viz., Class I and Class II aldolases. (W. J. Rutter, *Fed. Proc. Amer. Soc. Exp. Biol.* (1964): vol. 23, p 1248.) Class I aldolases utilize the ε-amino group of a Lys in the active site to form a Schiff base with one of the substrates, which activates the substrate as an aldol donor.

The mechanism for class I aldolases is illustrated in FIG. 1. The reaction is bimolecular and proceeds through covalent catalysis through multiple intermediates. An iminium ion or Schiff base forms that acts as an electron sink, which lowers the activation energy ($E_a$) for proton abstraction from Cα and subsequent enamine formation. The enamine acts as the carbon nucleophile, or aldol donor, which reacts with an aldehyde electrophile, the aldol acceptor, to form a new C—C bond. The Schiff base is then hydrolyzed and the product is released. The essence of the mechanism is the formation of the enamine which is the nascent carbon nucleophile.

Class II aldolases are metalloenzymes that facilitate enolate formation by coordination to the substrate's carbonyl oxygen. Transition state models have also been disclosed for aldol reactions involving metals. (H. E. Zimmerman et al., *J. Am. Chem. Soc.* (1957): vol. 79, p 1920.) However, the mechanism for Class II aldolases remains to be fully characterized.

A number of enzymes catalyze the aldol condensation. The mechanisms of these enzymes have been well characterized. (C. Y. Lai, et al., *Science* (1974): vol. 183, p 1204; and A. J. Morris et al., *Biochemistry* (1994) vol. 33, p 12291.) However, aldolase enzymes accept a relatively limited range of substrates (C. -H. Wong et al., *Enzymes in Synthetic Organic Chemistry* (Permagon, Oxford, 1994); M. D. Bednarski in *Comprehensive Organic Synthesis*, B. M. Trost, Ed.(Pergamon, Oxford, 1991), vol 2, pp. 455–473; C. F. Barbas III, et al., *J. Am. Chem. Soc.* (1990): vol 112, p 2013; H. J. M. Gijsen et al., *J. Am. Chem. Soc.* (1995): vol. 117, p 2947; C. -H. Wong et al., *J. Am. Chem. Soc.* (1995): vol. 117, p. 3333; L. Chen, et al., *J. Am. Chem. Soc* (1992): vol. 114, p 741.) Although natural aldolase enzymes display broad specificity with respect to the aldol acceptor, the aldol donor is usually limited to the natural substrate. The art of organic synthesis would benefit significantly if catalysts having the desired substrate specificity could be produced to order for catalyzing desired aldol addition reactions.

Non-enzymic base catalyzed aldol addition reactions are employed widely in organic chemistry to form new carbon-carbon bonds. Also, a variety of effective reagents have been developed to control the stereochemistry of the aldol. However, these reagents are stoichiometric and require pre-formed enolates and extensive protecting group chemistry. (C. H. Heathcock, *Aldrichim. Acta* (1990): vol. 23, p 99; C. H. Heathcock, *Science* (1981): vol. 214, p 395; D. A. Evans, *Science* (1988): vol. 240, p 420; S. Masamune, et al., *Angew. Chem. Int. Ed. Engl.* (1985): vol. 24, p 1; D. A. Evans, et al., *Top. Stereochem.* (1982): vol. 13, p 1; C. H. Heathcocket et al., in *Comprehensive Organic Synthesis*, B. M. Trost, Ed. (Pergamon, Oxford, 1991), vol. 2, pp. 133–319 (1991); and I. Paterson, *Pure & Appl. Chem.* (1992): vol. 64, 1821.) Recently catalytic aldol reactions that use pre-formed enolates have been developed, including the Mukaiyama cross-coupling aldol. (S. Kobayashi, et al., *Tetrahedron* (1993): vol. 49, p 1761; K. Furuta, et al., *J. Am. Chem. Soc.* (1991): vol. 113, p 1041; T. Bach, *Angew. Chem. Int. Ed. Engl.* (1994): vol. 33, p 417 and references therein; and E. M. Carreira, et al., *J. Am. Chem. Soc.* (1995): vol. 117, p 3649.)

For some reactions, the problem of complex intermediates may be solved by using relatively reactive compounds rather than the more usual inert antigens to immunize animals or select antibodies from libraries such that the process of antibody induction involves an actual chemical reaction in the binding site. (C. F. Barbas III, et al., *Proc. Natl. Acad. Sci. USA* (1991): vol. 88, p 7978 (1991); K. D. Janda et al., *Proc. Natl. Acad. Sci. USA* (1994): vol. 191, p 2532.) This same reaction then becomes part of the catalytic mechanism when the antibody interacts with a substrate that shares chemical reactivity with the antigen used to induce it.

One of the major goals of organic chemistry is to use the understanding of reaction mechanisms to design new catalysts. This is often not easy because one must address intermediates that are of high energy and complex structure. Antibody catalysts offer one potential solution to this problem in that they can be programmed by the experimenter to interact with the rate limiting transition state of a chemical reaction thereby lowering its energy and increasing the reaction rate. (R. A. Lerner, et al., *Science* (1991): vol. 252, p 659.) However, even here the ability of the experimenter to program the catalyst is usually limited to the more global aspects of the transition state rather than the detailed reaction mechanism. Thus, while one can deal with high energy charges, stereoelectronic, and geometrical features that appear along the reaction coordinate, the organization of multiple complex reaction intermediates remains difficult.

What is needed is a method for inducing antibodies that use the reaction mechanisms that give aldolases their efficiency but that take advantage of the range of substrates and stereochemical specificities available with antibodies. What is need is a strategy which would amalgamate the best features of the simple chemical and enzymatic approaches to the problem of forming carbon-carbon bonds via the aldol condensation which is, arguably, the most basic C—C bond forming reaction in chemistry and biology.

SUMMARY

The invention is directed to the generation of antibodies that catalyze the aldol reaction. The catalytic antibodies are generated by immunization with a reactive compound that covalently traps a Lysine (Lys) residue in the binding pocket of the antibody by formation of a stable vinylogous amide, i.e., a covalent antibody/hapten complex. The catalytic mechanism for these catalytic antibodies is disclosed to mimic the catalytic mechanism employed by natural class I aldolase enzymes.

The same reaction mechanism employed to form the covalent antibody/hapten complex is also employed to catalyze the aldol reaction. During catalysis, the antibodies use the ε-amino group of Lys to form an enamine with ketone substrates and then use this enamine as a nascent carbon nucleophile to attack the second substrate, an aldehyde, to form a new carbon-carbon bond. The catalytic antibodies disclosed herein are characterized by their broad substrate specificity and their ability to control the diastereofacial selectivity of the reaction in both Cram-Felkin and anti-Cram-Felkin directions.

More particularly, one aspect of the invention is directed to antibody molecules or molecules containing antibody combining site portions that catalyze an aldol addition reaction between an aliphatic ketone donor and an aldehyde acceptor. These antibodies are characterized by having a lysine with an ε-amino group. They are further characterized by being subject to inhibition with the 1,3-diketone hapten by formation of a complex between the 1,3-diketone hapten and the ε-amino group of the lysine of the catalytic antibody. The complex being may be a stable covalent vinylogous amide, a conjugated enamine, or a Schiff base. In a preferred embodiment, the antibody molecules control the diastereofacial selectivity of the aldol addition reaction in both Cram-Felkin and anti-Cram-Felkin directions. Preferred aliphatic ketone donors include compounds represented by the following structures:

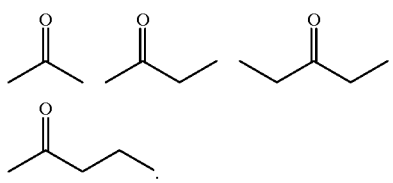

Preferred aldehyde acceptor include compounds represented by the following structures:

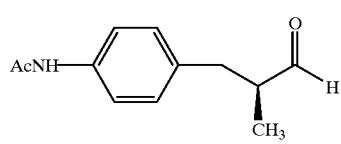

6

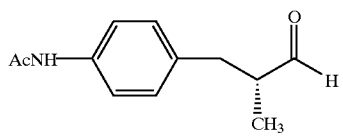

7

-continued

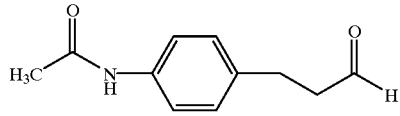

12

Another aspect of the invention is directed to molecules of claim 1 what are secreted by hybridoma 38C2, having ATCC accession number HB 12005 or by hybridoma 33F12, having ATCC accession number HB 12004.

Another aspect of the invention is directed to cells that when cultured in a medium produce the above indicated monoclonal antibody molecules or molecules containing antibody combining site portions that catalyze an aldol addition reactions. In a preferred embodiment, the cells are to a type that secrete into the culture medium the monoclonal antibody molecules or molecules containing antibody combining site portions. Hybridoma cells are a preferred embodiment, viz., hybridoma cells of hybridoma 38C2, having ATCC accession number HB 12005 and hybridoma cells of hybridoma 33F12, having ATCC accession number HB 12004.

A further aspect of the invention is directed to a method for catalyzing an aldol addition reaction between an aliphatic ketone donor and an aldehyde acceptor. The method begins by admixing a catalytically effective amount of the monoclonal antibody molecules or molecules containing antibody combining site portions described above with the aliphatic ketone donor and said aldehyde acceptor in an aqueous medium to form a reaction admixture. After the reaction admixture is formed, it is maintained for a period of time sufficient for the antibody molecules or molecules containing antibody combining site portions to catalyze the aldol addition reaction between the aliphatic ketone donor and the aldehyde acceptor. In a preferred mode of the above synthetic method, the antibody molecules or molecules containing antibody combining site portions thereof are secreted by hybridoma 38C2, having ATCC accession number HB 12005 or by hybridoma 33F12, having ATCC accession number HB 12004.

An alternative mode of the invention is directed to a process for carrying out an aldol addition reaction by forming a reaction mixture by admixing an aliphatic ketone donor, an aldehyde acceptor, and a catalytically effective amount of monoclonal antibodies or paratope-containing portions of the monoclonal antibodies in an aqueous medium at a pH value between about 6 and 10. The monoclonal antibodies or paratope-containing portions thereof are of a type which include a lysine with an ε-amino group which reacts with the aliphatic ketone donor to form an enamine intermediate. After the reaction mixture is formed, it is maintained under biological reaction conditions for a time period sufficient for the enamine intermediate to react with the aldehyde acceptor to form an aldol addition product.

Another aspect of the invention is directed to a method for preparing cells that when cultured in a medium produce antibody molecules or molecules containing antibody combining site portions that catalyze an aldol addition reaction between an aliphatic donor and a aldehyde acceptor. The method starts by immunizing an animal with an immunogen that includes a 1,3-diketone hapten. Then the animal is maintained for a time period sufficient for it to secrete antibodies that immunoreact with the haptenic ligand. Then genes that encode antibody molecules or molecules containing antibody combining site portions are transferred from antibody-producing cells of the maintained, immunized animal into host cells to form hybrid cells. The hybrid host cells contain genes from at least two sources. The formed hybrid cells have two characteristics, viz.,(i) they produce antibody molecules or molecules containing antibody combining site portions from the transferred genes when cultured and (ii) they can be cultured substantially indefinitely. Then, the hybrid cells are cultured in an appropriate culture medium for a time period sufficient for them to produce antibody molecules or molecules containing antibody combining site portions. Next, antibody molecules or molecules containing antibody combining site portions are recovered from the cultured hybrid cells. Then, the obtained antibody molecules or molecules containing antibody combining site portions are screened for catalytic activity directed to the aldol addition reaction. And finally, clones are grown of the identified hybrid cell that produces antibody molecules or molecules containing antibody combining site portions that catalyze the aldol addition reaction between the aliphatic donor and the aldehyde acceptor. Preferred hybrid cells are hybridoma cells.

BRIEF DESCRIPTION OF THE DRAWINGS

FIG. 2). Hapten 5, 5 eq, was added to 20 mM solutions of each antibody in PBS buffer (pH=7.5) in a microtiter plate format. Antibodies with aldolase catalytic activity presented the typical absorption maximum of the vinylogous amide at 316 nm (example shown in top line), whereas none of the inactive antibodies did (example shown in bottom line). Two antibodies out of 20 formed the vinylogous amide intermediate (bottom right structure; FIG. 2) and were subsequently determined to be catalytic. This efficient method affords rapid screening of a large number of antibodies.

FIG. 2). A fixed concentration (100 mM) of hapten 5 was added to the indicated concentrations of antibody 33F12. The antibody enamine complex could easily be detected at an antibody concentration as low as 2 mM. FIG. 2).

DETAILED DESCRIPTION

Figure 1:
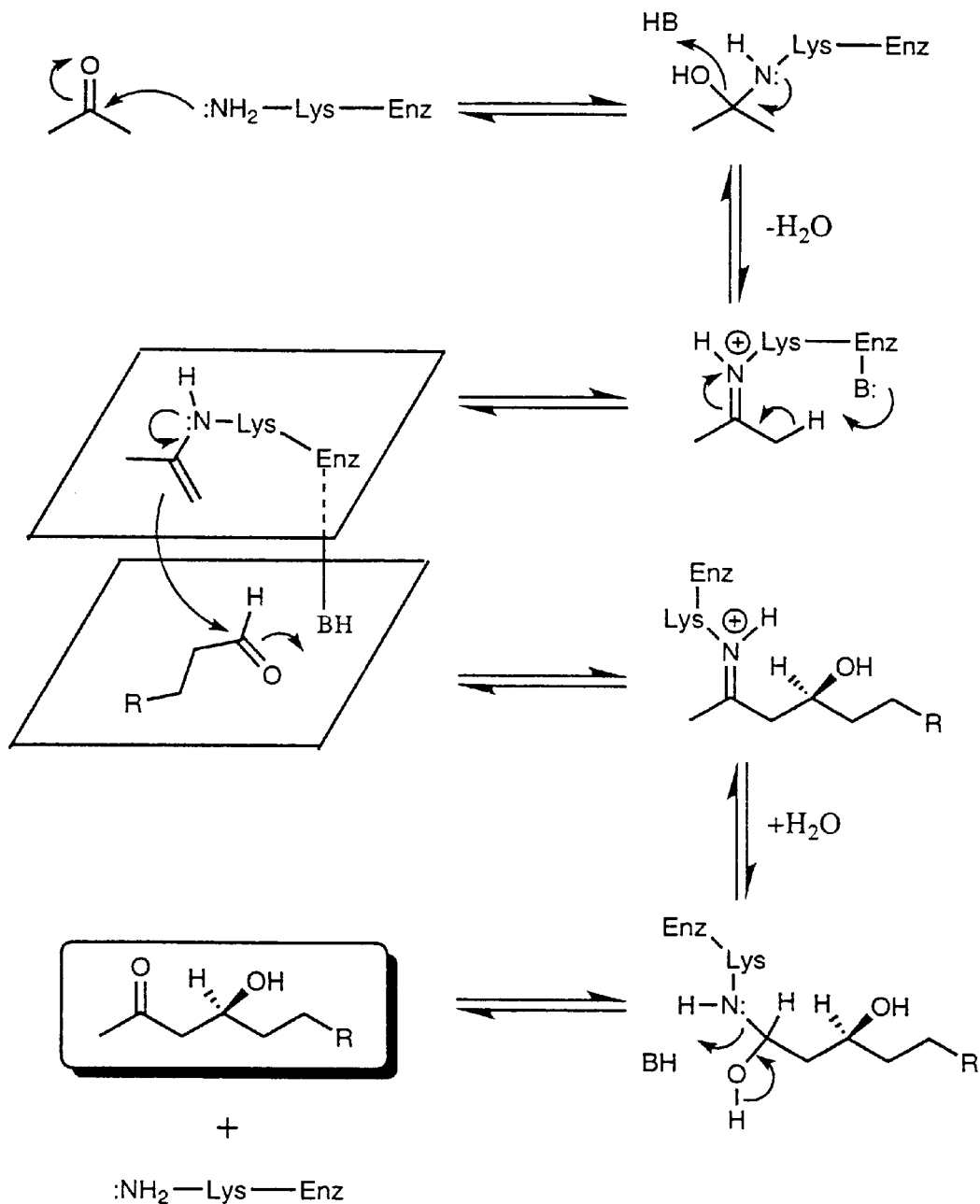
FIG. 1 illustrates the general mechanism of a class I aldolase catalyzed aldol addition reaction (Lai et al. Science 183, 1204 (1974); Morris et al. Biochemistry 33, 12291 (1994); Rutter et al. Fed. Proc. Amer. Soc. Exp. Biol. 23, 1248 (1964)) (Enz, enzyme; B, base).
Figure 2:
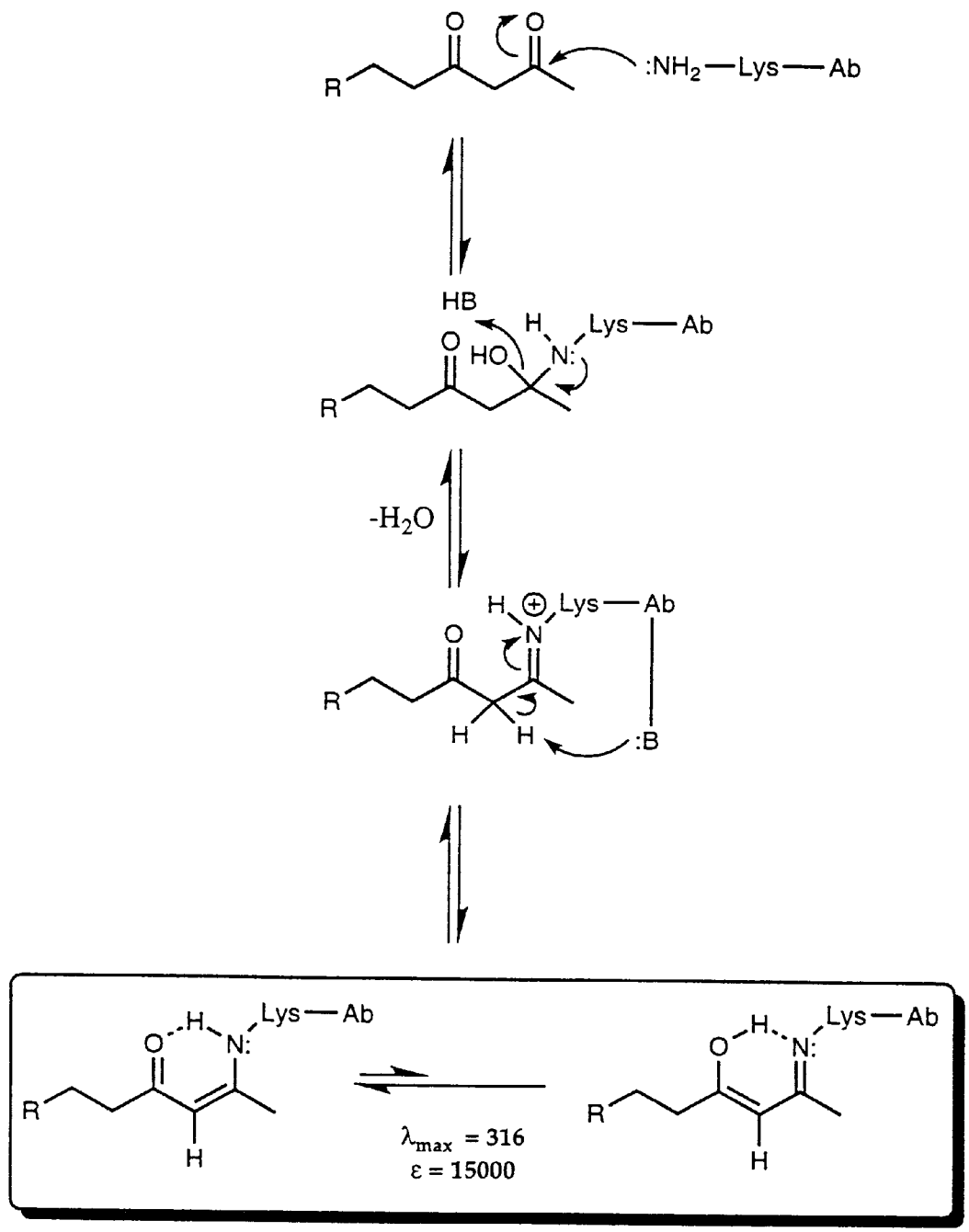
FIG. 2 illustrates the mechanism of trapping the essential $\epsilon$-amino group of a Lys residue in the antibody (Ab) binding pocket using the 1,3-diketone hapten 5. The formation of the stable covalent vinylogous amide (bottom right drawing) can be detected at $\lambda=316$ nm($\epsilon$ is the extinction coefficient= 15000). $R=p(HOOC(CH_2)_3 CONH)C_6H_4—$.

The haptens are designed both to trap the requisite Lys residue in the active site of the antibody, to induce the antibody to form the essential enamine intermediate, and to induce the appropriate binding sites for the two substrates to overcome the entropic barrier intrinsic to this bimolecular reaction. The simple 1,3-diketone hapten 5 provides elements of both a chemical and entropic trap, as illustrated in FIG. 2. In water, the keto-form of the hapten shown predominates over the enol-form at a ratio of 3 to 1. (M. Moriyasu, et al., *J. Chem. Soc. Perkin Trans. II* (1986): p 515.) The reaction coordinates of the aldol addition and the reaction mechanism expected when the hapten interacts with some antibodies share several common intermediates. In both cases, a tetrahedral carbinolamine intermediate forms that dehydrates to afford the cationic iminium that tautomerizes to the enamine. It was expected that antibodies induced according to the haptenic reaction mechanism would stabilize the analogous transition states and cationic intermediates along the reaction coordinate of the aldol reaction. The driving force for the reaction of the 1,3-diketone hapten with the antibody is the formation of a stable covalent vinylogous amide or conjugated enamine between the hapten and the ε-amino group of lysine. Calculations using the Woodward rules for enones indicated that the vinylogous amide would have an absorption maximum in an appropriate ultraviolet spectral region to allow for its identification, $\lambda_{max}$=318 nm. (E. Pretsch, et al., *Tables of Spectral Data for Structure Determination of Organic Compounds*, (Springer-Verlag, Berlin, ed. 2, 1989), p. U20.) The stability and spectral characteristics of this type of compound were previously noted in the studies of acetoacetate decarboxylase by Westheimer and co-workers. (W. Tagaki, et al., *Biochemistry* (1968): vol. 7, p 905.) We expected an entropic advantage by incorporation of the second substrate (aldol acceptor) in the diketone chemical trap. It has been suggested that entropic effects can provide as much $10^8$ to $10^{11}$ to the rate acceleration of natural enzymes. (M. I. Page et al., *Proc. Natl. Acad. Sci. U.S.A.* (1971): vol. 68, p 1678.)

Figure 3:
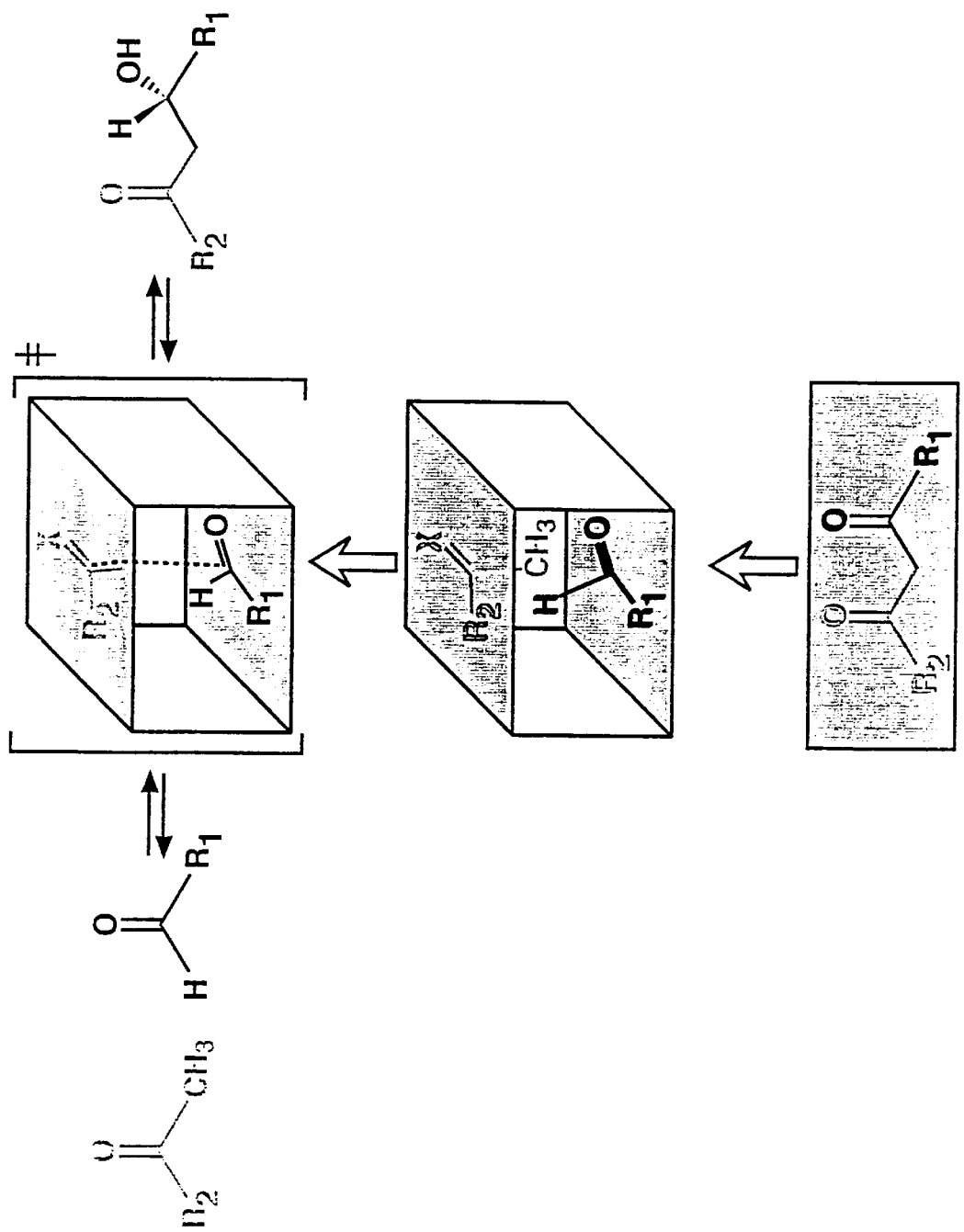
FIG. 3 illustrates the 1,3-diketone hapten structure contains the elements of a chemical and entropic trap. The binding pocket induced with the hapten 5 does not preclude attainment of a reasonable Heathcock angle for attack of the aldol donor on the acceptor. A proper attack geometry is attained by simple rotation of both enamine and aldehyde faces.

A preferred example of the disclosed reaction is the aldol addition of acetone to 3-phenylpropionaldehyde derivatives. The second substrate is represented by the 3-phenylpropiononyl portion of the hapten. The tethering of the two substrates in the diketone hapten would present a substrate complex wherein the Heathcock angle for attack of the enamine on the aldehyde would be distorted to the extreme of 90° in the rate determining transition state of C—C bond formation. (E. P. Lodge et al., *J. Am. Chem. Soc.* (1987): vol. 109, 3353.) This was not expected nor did it prove to be a major impediment in the catalytic reaction because rotation of both enamine and aldehyde faces should provide a reasonable Heathcock angle, as illustrated in FIG. 3.

The central concept of the invention disclosed herein is that catalysts employing a covalent reaction mechanism can be induced by immunization with reactive compounds. Examples of this principle provided herein include but are not limited to Schiff base or enamine mechanisms. This approach is particularly useful whenever the chemistry to be accomplished is beyond that easily achieved by even a concert of noncovalent interactions.

EXAMPLES

Figure 4:
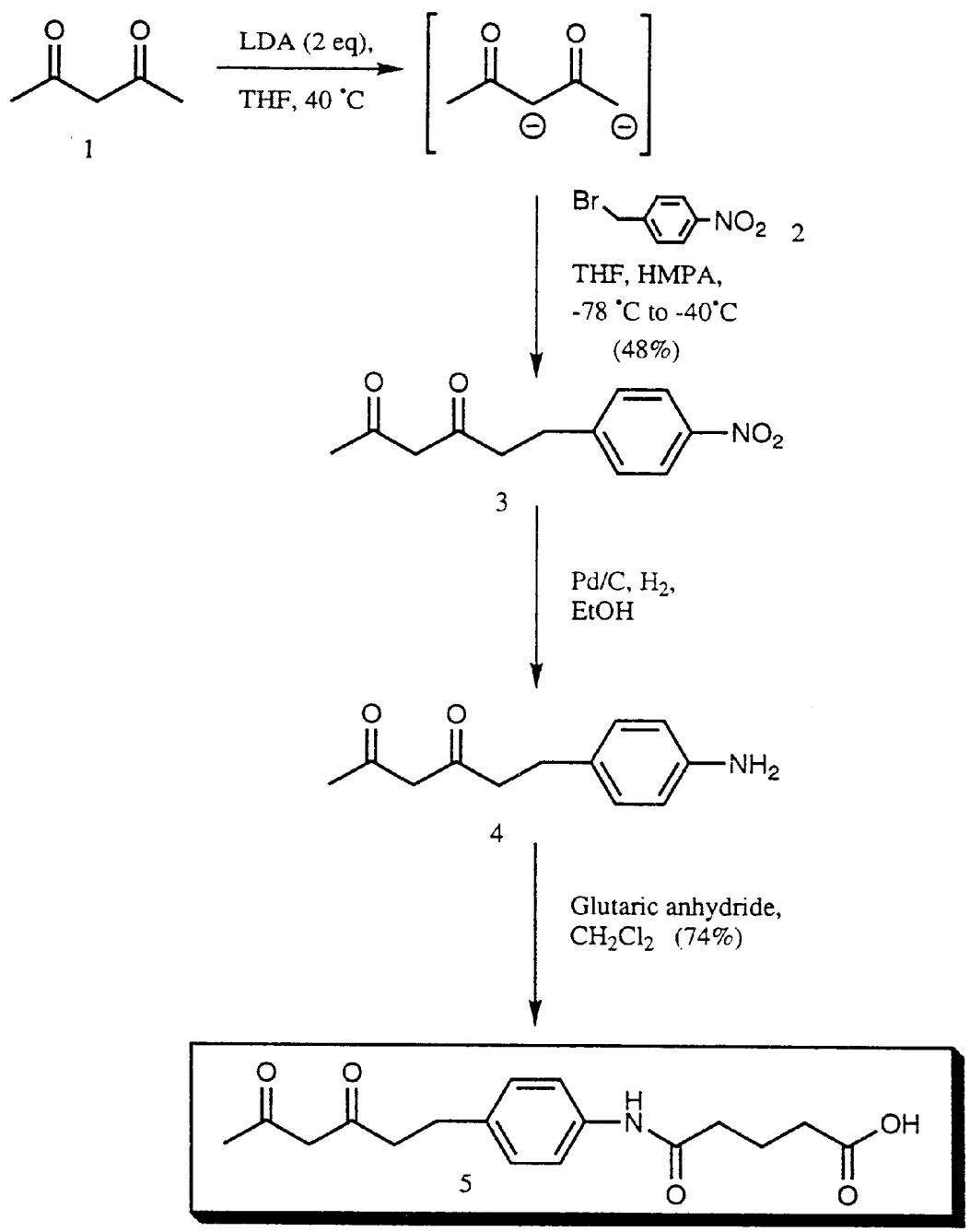
FIG. 4 illustrates the synthesis of hapten 5. The steps are as follows: (a) LDA [2 equivalents(eq)], THF, 40° C., 1 hour; (b) 4-nitrobenzylbromide, hexamethylphosphoramide, −78° C. to −40° C., 48% yield; (c) (i) Pd/C, H2, ethanol; (ii) glutaric anhydride, $CH_2Cl_2$, 74% yield.

Synthesis of compound 3 (FIG. 4)

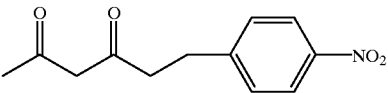

3

Compound 3: Diisopropylamine (1.43 mL, 2.1 eq), distilled over CaH$_2$, was dissolved in dry THF (80 mL). The solution was cooled to 0° C. and 1.6 M butyllithium in hexane (6.4 mL, 2.1 eq) was slowly added. The colorless solution of LDA (lithiumdiisopropylamide) was kept at 0° C. for 30 min and hexamethylphosphoramide (0.8 mL, 0.9 eq) was added. Freshly distilled 2,4-pentanedione (0.5 mL, 1.0 eq; Aldrich), dissolved in dry THF (20 mL) was added slowly. The mixture was heated to 40° C. for 1 h. The yellowish solution of the dianion was cooled to −78° C. and 4-nitrobenzylbromide (1.052 g, 1.0 eq; Aldrich Chemical company), dissolved in dry THF (20 mL), was added slowly. The temperature was slowly (~20 min) raised to −40° C. (TLC control: AcOEt/Pet. Ether 1:3). The reaction was poured into an ice-cold mixture of CH$_2$Cl$_2$ and a saturated solution of NH$_4$Cl (100 mL). After phase separation, the aqueous phase was reextracted with CH$_2$Cl$_2$. The combined organic phases were dried over MgSO$_4$ and the solvent was evaporated. The residue was purified by column chromatography (SiO$_2$, 230–400 mesh, AcOEt/Pet. Ether 1:3) to afford 3 (544 mg, 48%) as a yellowish solid, which can be recrystallized in AcOEt/Pet. Ether 1:3. $^1$H NMR (CDCL$_3$, 300 MHZ): enol form d 8.12–8.19 (m, 2H), 7.33–7.41 (m, 2H), 5.47 (s, 1H), 3.05 (t, J=7.5, 2H), 2.65 (t, J=7.5, 2H), 2.08 (s, 3H); $^{13}$C NMR (CDCl$_3$, 125 MHz): enol form d 192.7, 190.3, 148.5, 129.2, 123.7, 100.1, 39.2, 30.9, 24.5; partial keto form d 146.5, 57.7, 44.2, 28.9; IR (neat) n$_{max}$ 3078, 2928, 2853, 1706, 1600, 1516, 1343, 1108, 854 cm$^{-1}$; MS m/z (relative intensity) 236 (M+H$^+$, 100); C$_{12}$H$_{13}$NO$_4$ (235.239).

Synthesis of diketone hapten 5 (FIG. 4)

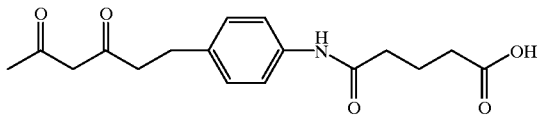

5

Compound 5: The diketone 3 (100 mg, 0.43 mmol) was dissolved in EtOH (10 mL). 10% Pd/C (45 mg, 0.1 eq) was added and the mixture was hydrogenated for 45 min under strong agitation (TLC: CH$_2$Cl$_2$/Et$_2$O 1:3). The slur was filtered through Celite, washed with CH$_2$Cl$_2$ (~50 mL) and dried over MgSO$_4$. Evaporation of the solvent gave the crude amine 4, which was redissolved in CH$_2$Cl$_2$ (15 mL). The solution was cooled to 0° C. and glutaric anhydride (53 mg, 1.1 eq) was added. The mixture was stirred at rt for 1.5 h (TLC: CH$_2$Cl$_2$/Et$_2$O 1:3). The solution was extracted with 0.2N NaOH. The aqueous phase was acidified to pH=1.0 with 2N HCl and extracted 3 times with AcOEt (15 mL). The combined organic phases were dried over MgSO$_4$ and the solvent was evaporated to afford 5 (100 mg, 74%) as a white solid. $^1$H NMR (CDCl$_3$, 500 MHz): enol form d 8.08 (s, 1H), 7.39–7.42 (m, 2H), 7.06–7.10 (m, 2H), 5.47 (s, 1H), 2.86 (t, J=8.1, 2H), 2.54 (t, J=8.1, 2H), 2.39–2.44 (m, 4H), 2.03 (s, 3H), 1.98–2.04 (m, 2H); keto form d 8.13 (s, 1H), 7.39–7.42 (m, 2H), 7.06–7.10 (m, 2H), 3.56 (s, 2H), 2.78–2.85 (m, 4H), 2.39–2.44 (m, 4H), 2.19 (s, 3H), 1.94–1.98 (m, 2H); $^{13}$C NMR (CDCl$_3$, 125 MHZ): enol form d 193.3, 191.3, 178.0, 171.3, 136.7, 135.9, 128.7, 120.3, 100.1, 36.9, 36.0, 33.0, 30.8, 24.8, 20.6; partial keto form d 57.8, 45.1, 32.9, 28.7, 19.6; IR (KBr) n$_{max}$ 3325, 3113, 3044, 2935, 1696, 1658, 1602, 1531, 1413, 1311, 918, 830, 683 cm−1; MS m/z (relative intensity) 320 (M+H$^+$, 92); C$_{17}$H$_{21}$NO$_5$ (319.357). Note: Around 83% of the diketone 5 is in the keto form in CHCl$_3$.

Coupling of hapten to carrier protein

Hapten 5 was coupled to the commonly used carrier protein Keyhole limpet hemocyanin according to the conditions as specified in Harlow et. al. *Antibodies: A Laboratory Manual*, Cold Spring Harbor Laboratory, 1988, 79.

Production of antibodies from hybridoma cell lines

After immunization of 129 G$^{fX+}$ mice (Scripps Research Institute), 20 hybridomas producing antibodies to 5 were obtained with standard methods as described in G. Kohler et. al. *Nature* 256, 495 (1975). Antibodies from each cell-line were then purified by ammonium sulfate precipitation, anion exchange, and protein-G affinity chromatography as described in V. E. Gouverneur et al., Science 262, 204 (1993); 20 antibodies were isolated.

Figure 5:
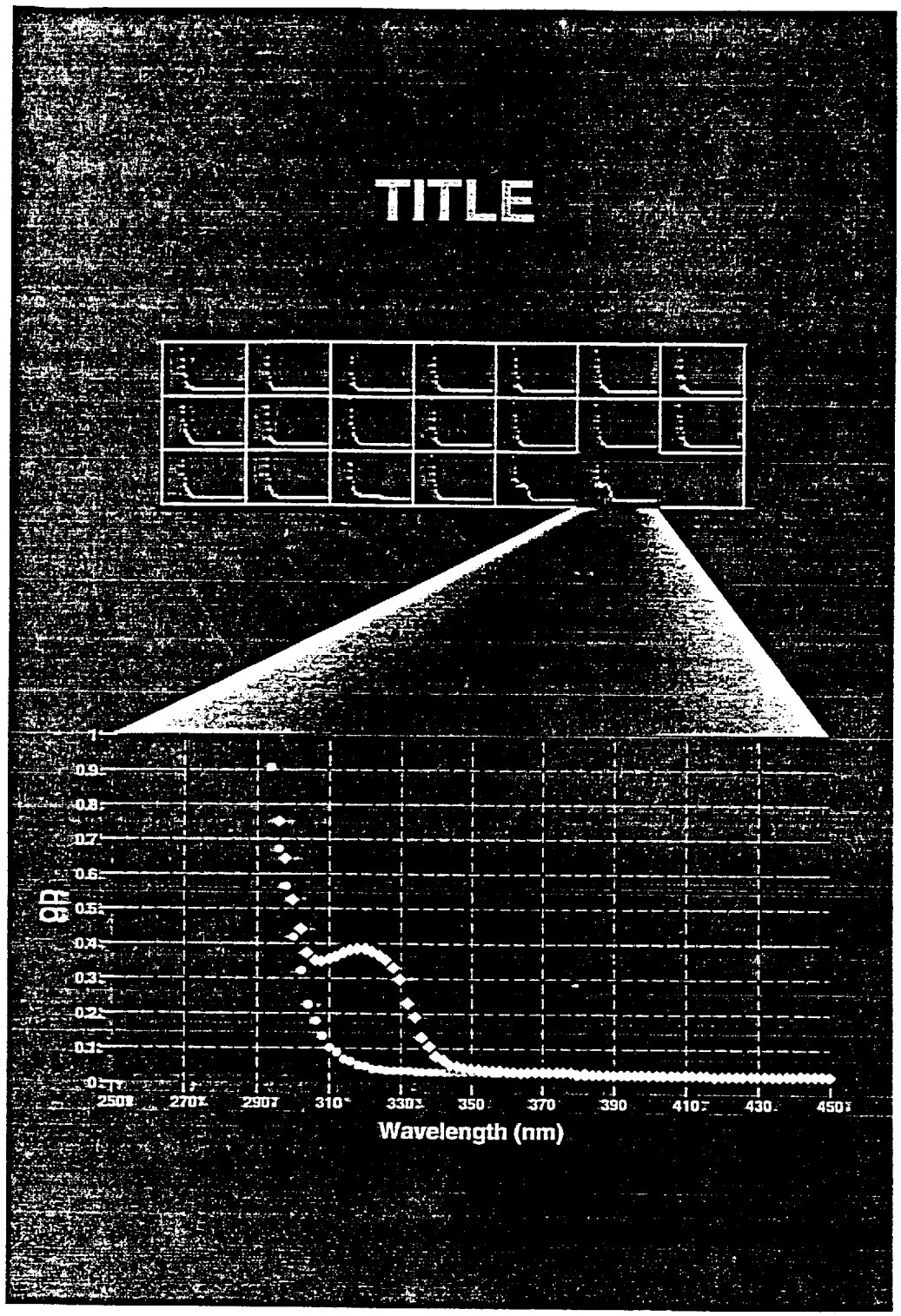
FIG. 5 illustrates the screening of antibodies for the formation of the vinylogous amide intermediate (bottom right structure.

Screening of the antibodies (FIG. 5)

All 20 antibodies were screened in a microtiter plate assay for their ability to form the proposed stable vinylogous amide, as shown in FIG. 2, by incubation of 20 mM antibody with 100 mM of the diketone hapten 5 (FIG. 5). Two antibodies, 38C2 and 33F12, demonstrated a strong absorption maximum at 316 nm characteristic of the proposed vinylogous amide, as shown in FIG. 2, approximating the calculated absorption maximum in the absence of protein of 318 nm (FIG. 5). Incubation of 5 with lysine under identical conditions resulted in no increase in absorbance.

Figure 6:
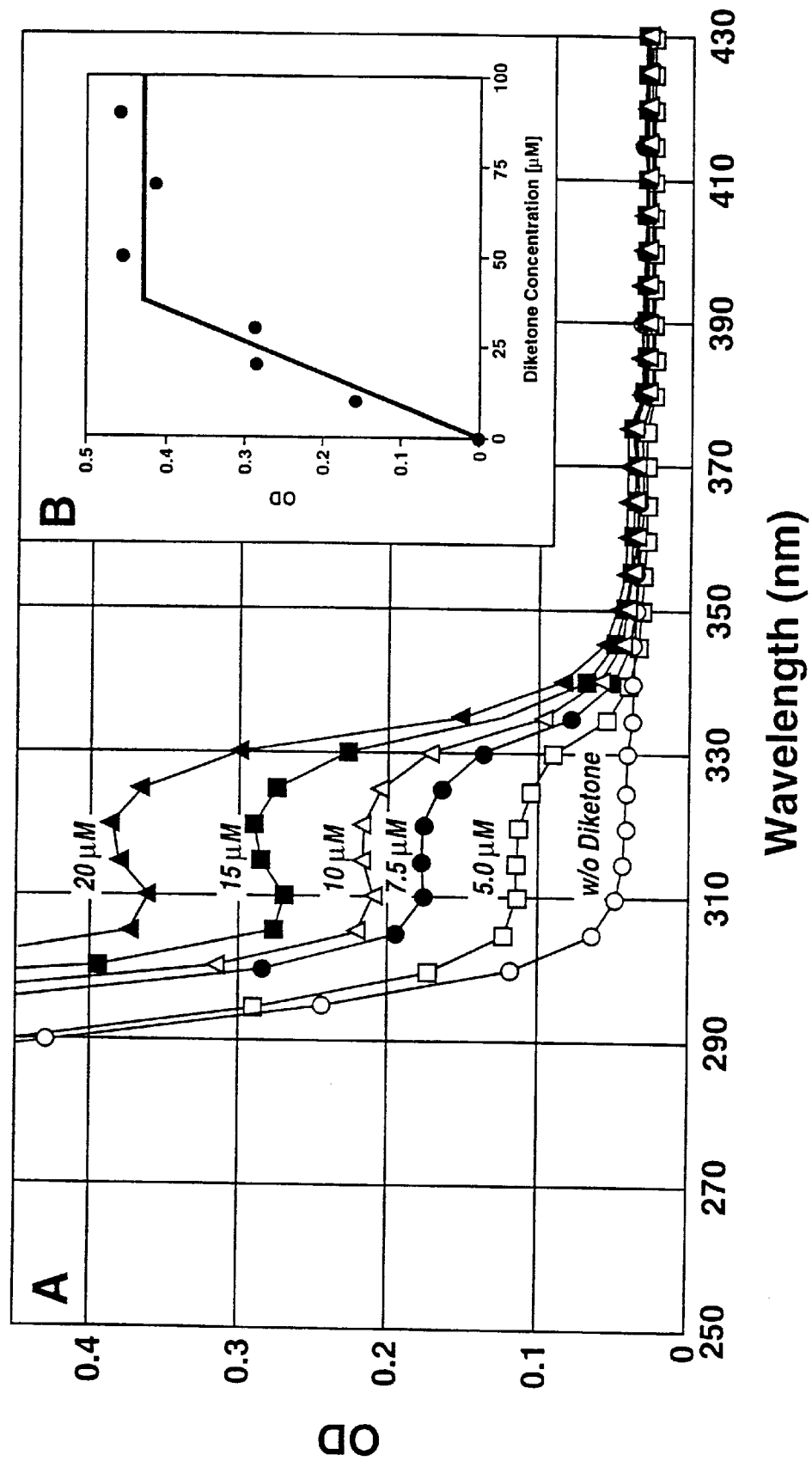
FIG. 6(A) illustrates the determination of the extinction coefficient of the vinylogous amide intermediate (bottom right structure.
FIG. 6(B) illustrates that the active sites of antibody 38C2 were titrated with acetylacetone. The antibody concentration (20 mM) was fixed. Acetylacetone, (0 to 4.5 eq), was added and the absorption measured at 316 nm. The intersection of the two lines corresponds to a ratio of 1.9 of acetylacetone to antibody 38C2, indicating that both binding sites of the antibody form the enamine adduct (bottom right structure.

Determination of the extinction coefficient (FIG. 6A)

The extinction coefficient of the antibody-enamine complex was determined to be 15000 cm$^{-1}$M$^{-1}$ after subtraction of the absorbance of the antibody (FIG. 6A), approximating that observed in the reaction of acetopyruvate with the enzyme acetoacetate decarboxylase, 19000 cm$^{-1}$M$^{-1}$.(W. Tagaki, et al., *Biochemistry* (1968): vol. 7, p 905.)

Determination of stoichiometry of antibody/enamine complex via titration with acetylacetone (FIG. 6B)

Because the antibodies are expected to form an enamine with acetone in the synthetic reaction, observation of the vinylogous amide chromophore should not be dependent on the aldol acceptor (benzyl) portion of the hapten. We tested acetylacetone as the minimal diketone expected to generate the chromophore. Both antibodies reacted with this compound and produced the expected absorbance spectrum. To determine the stoichiometry of the antibody/enamine complex, a titration of the antibody with acetylacetone was carried out, according to the conditions of Tagaki et al. *Biochemistry* 7, 905, 1968. Assuming the reaction that forms the enamine is irreversible, the stoichiometry of the titration should correspond to the concentration of antibody active sites. The titration gives a ratio of acetylacetone to antibody of 1.9, indicating that each of the two identical antigen binding sites of the antibody form the vinylogous amide adduct (FIG. 6B). Catalysis of the formation of the vinylogous amide was essentially complete upon mixing of the antibody with hapten and sufficiently rapid that determination of the rate of this reaction will require stopped-flow kinetic studies.

Figure 9:
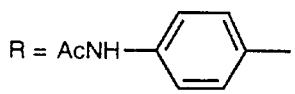
FIG. 9 illustrates the substrate specificity of antibody 38C2. The kinetic parameters kcat and Km of each reaction were calculated with respect to the aldehyde (12 or 6+7). The aldol donors (acetone, 2-butanone, 3-pentanone, 2-pentanone and acetaldehyde) were fixed at a constant concentration of 5% v/v in each experiment. Products 15/16 and 18/19 were formed at ratios 94 to 4 and 73 to 27, respectively.

Addition of aldol donor to aldehydes in presence of antibody to produce β-hydroxy ketone (FIG. 9)

Antibodies 38C2 and 33F12 were assayed for their ability to catalyze the addition of aldol donors (acetone, 2-butanone, 3-pentanone and 2-pentanone) to aldehydes 6, 7 and 12 (FIG. 9). A typical procedure is as follows: 100 μL of pH 7.5 buffer solution with 0.2 mM EDTA, 100 mM tris and approx. 5% v/v (volume donor/volume solvent) aldol donor concentration were introduced into n-wells of a microtiter plate. Antibodies 38C2 and 33F12 (100 μL, 34 μM, Tris buffer, pH=7.5) were added to different wells; 100 ml buffer only was added to the remaining wells, which were the blanks. The ultraviolet absorbance was measured at 340 nm every 15 min for 24 hours. The absorbance of the blanks was subtracted from the catalyzed reactions, and the rate was determined using ε=6220 M$^{-1}$cm$^{-1}$. Antibodies 38C2 and 33F12 had the same k$_{cat}$=4.53 10$^{-3}$ min$^{-1}$, which correlates well with the HPLC measurements. Consumption of and production of the β-hydroxy ketone were monitored by reversed-phase high-performance liquid chromatography (HPLC) as follows: a RP-C18 column (MICROSORB-MV, 0.45 cm by 22 cm) was used with an isocratic program of 75/25; H$_2$O (0.1% trifluoroacetic acid)/ H2O:acetonitrile 1:1, at 1.5 ml/min, monitored at 254 nm. The retention times of the aldehyde 12 and the aldol product (13,14) are 6.35 and 8.78 min, respectively. For kinetic studies the ketone concentration was fixed at 5% v/v and the concentration of 12 or 6+7 was varied from 30 to 200 μM in the study of the aldol addition reaction. Antibodies were also assayed after an additional purification step over an anion exchange column with identical results.

Figure 13:
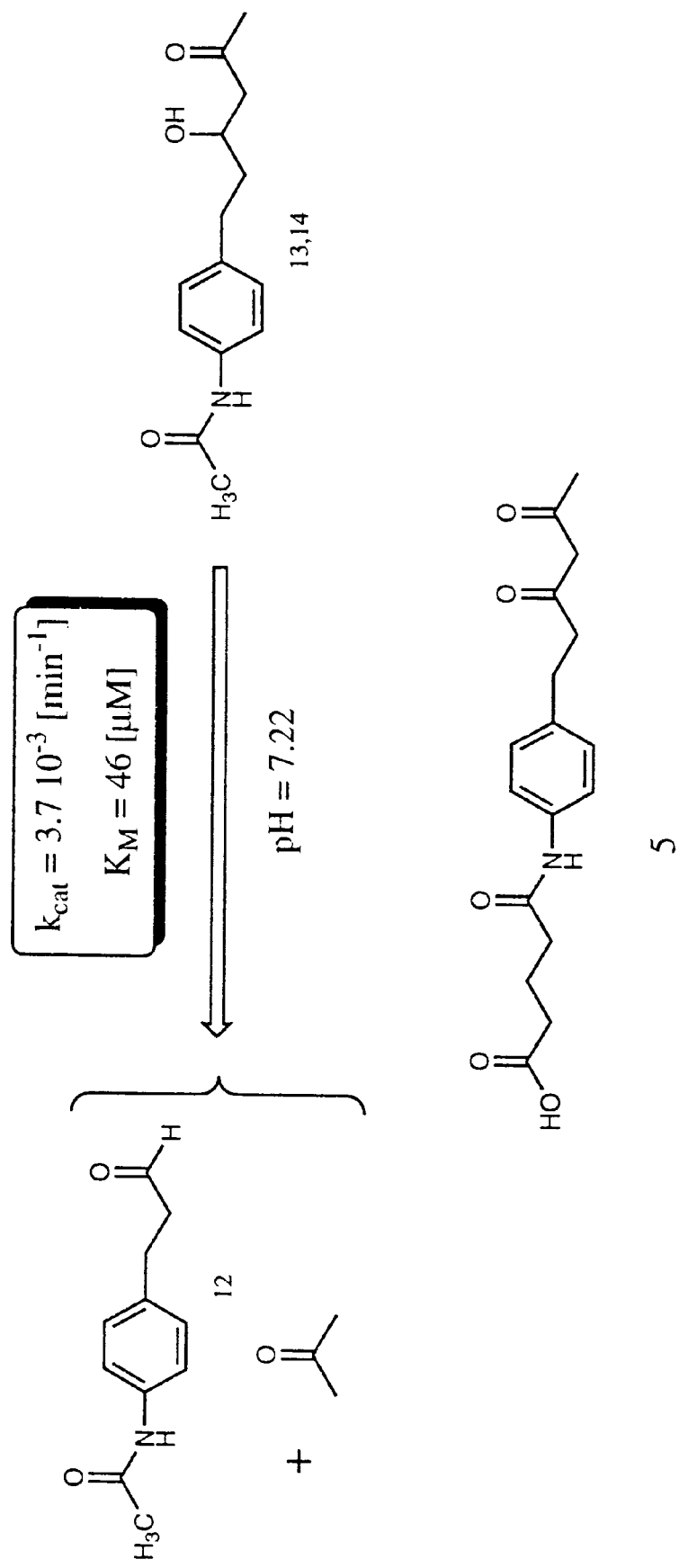
FIG. 13 illustrates retrograde aldol reaction kinetics using antibody 38C2 and 33F12 derived from hapten 5 and product 13/14 to form aldehyde 12 and acetone. Procedure as follows: A solution, 100 ml, pH=7.22, containing 0.2 mM EDTA, 100 mM Tris, 4.5 mg yeast alcohol dehydrogenase, 0.43 mg NADH and 4 mM b-hydroxy ketone 4 was introduced into four wells of a microtiter plate. Antibodies 38C2 and 33F12 (100 ml, 34.6 mM, tris buffer, pH=7.22) were added to two different wells; 100 ml buffer only was added to the remaining wells, which were the blanks. The ultraviolet absorbance was measured at 340 nm every 15 min for 24 hours. The absorbance of the blanks was subtracted from the catalyzed reactions, and the rate was determined using $\epsilon=6220$ M−1 cm−1. Retrograde aldol reaction at pH=7.22: $K_{cat}=3.7 \cdot 10^{-3}$ [$min^{-1}$]; $K_M=46$ [$\mu M$].

Analysis of Retroaldol reaction (FIG. 13)

Both antibodies demonstrated catalysis of the aldol addition that followed Michaelis-Menten kinetics. The ability of these two antibodies to generate acetone and aldehyde 3 from the β-hydroxy ketone 4 in the retro-aldol reaction was monitored by following the decrease in UV absorbance at 340 nm in a coupled enzymatic assay with alcohol dehydrogenase and β-nicotinamide adenine dinucleotide, reduced form (NADH). A typical procedure is as follows: A solution, 100 ml, pH=7.5, containing 0.2 mM EDTA, 100 mM Tris, 4.5 mg yeast alcohol dehydrogenase, 0.43 mg NADH and 4 mM β-hydroxy ketone (13,14) was introduced into four wells of a microtiter plate. Antibodies 38C2 and 33F12 (100 ml, 34.6 mM, tris buffer, pH=7.5) were added to two different wells; 100 ml buffer only was added to the remaining wells, which were the blanks. The ultraviolet absorbance was measured at 340 nm every 15 min for 24 hours. The absorbance of the blanks was subtracted from the catalyzed reactions, and the rate was determined using ε=6220 M$^{-1}$ cm$^{-1}$. Antibodies 38C2 and 33F12 had the same k$_{cat}$=4.53 10$^{-3}$ min$^{-1}$, which correlates well with the HPLC measurements. Production of aldehyde 12 was monitored by its subsequent reduction by alcohol dehydrogenase and consumption of NADH. The retro-aldol reaction was also studied by HPLC and the same results were obtained. The Michaelis constant KM and catalytic rate constant kcat values were 54 uM and 4.4×10−3 min−1, respectively for antibody 38C2. The remaining 18 antibodies were unable to catalyze the synthetic and retrosynthetic aldol reactions, indicating that only those that formed the critical intermediate were active (FIG. 13).

Substrate inhibition on aldol reaction

The ability of hapten 5 and acetylacetone to inhibit the aldol reaction was characterized to involve an enamine intermediate. When 3 equivalents of either hapten 5 or acetylacetone were provided, prior to the aldol addition or retro-aldol assays, catalytic activity was completely inhibited, showing that trapping of the enamine intermediate with the 1,3-diketones precludes catalysis involving the Lys ε-amino group. To establish that enamine formation with the hapten in the trapping assay and acetone in the catalytic assay are dependent on the same Lys residue, antibodies incubated with acetone were treated with NaBH4. Reduction with NaBH4 of the imine intermediate formed in the reaction of acetone with the Lys ε-amino group in the antibodies would result in irreversible isopropylation of the essential amine (Chang et. al. Science 183, 1204 (1974); A. J. Morris et. al. Biochemistry 33, 12291 (1994)). Following treatment the antibodies were completely inactivated in their ability to form the vinylogous amide with the diketones. These experiments provide evidence that the reaction mechanism and residues induced with the 1,3-diketone hapten are the same as those recruited in the catalytic reactions. The antibody aldolases showed a broad pH optimum between 6 and 10 approximating that observed with natural class I aldolases.

Efficiency of aldol donors

The antibodies accept acetone, fluoroacetone, chloroacetone, 2-butanone, 3-pentanone, 2-pentanone, and dihydroxyacetone, as aldol donor substrates. In reactions with 2-butanone and 2-pentanone the antibodies exhibit some control of the regioselectivity of the aldol addition by preferential formation of the most substituted enamine. The relative efficiency of catalysis with these substrates decreases 42-fold as reflected by kcat/KM in the acetone to pentanone series (FIG. 9, entries 1, 3 to 5). Antibodies failed to accept acetaldehyde as a donor which demonstrates that the aldol addition is directed with a ketone as the aldol donor. The two catalysts we have isolated are restricted in that they direct the aldol addition with acetone or aliphatic ketones as donors and 3-phenylpropionaldehyde derivatives as acceptors.

Aldol reaction with 3-phenylpropionaldehyde acceptor (6+7) to form β-hydroxy ketone products (9,10)

Figure 8:
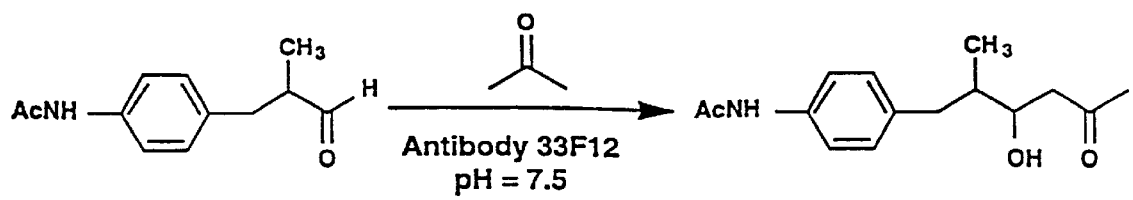
FIG. 8 illustrates the aldol addition reaction of aldehyde (6+7) and acetone as monitored over a 36 hour period in the presence of 1.5% catalyst. The catalyst showed multiple turnovers (~2 turnovers/hour) and virtually no product inhibition. A 90% conversion could be obtained in the presence of excess acetone (5% v/v) to minimize the retro-aldol reaction. The perfect mass balance (top line) indicates that no side reactions, such as elimination or polymerization, occurred over that period. Thus, the antibody catalyzed aldol reaction is an exceptionally mild method of C—C bond formation.
Figure 8:
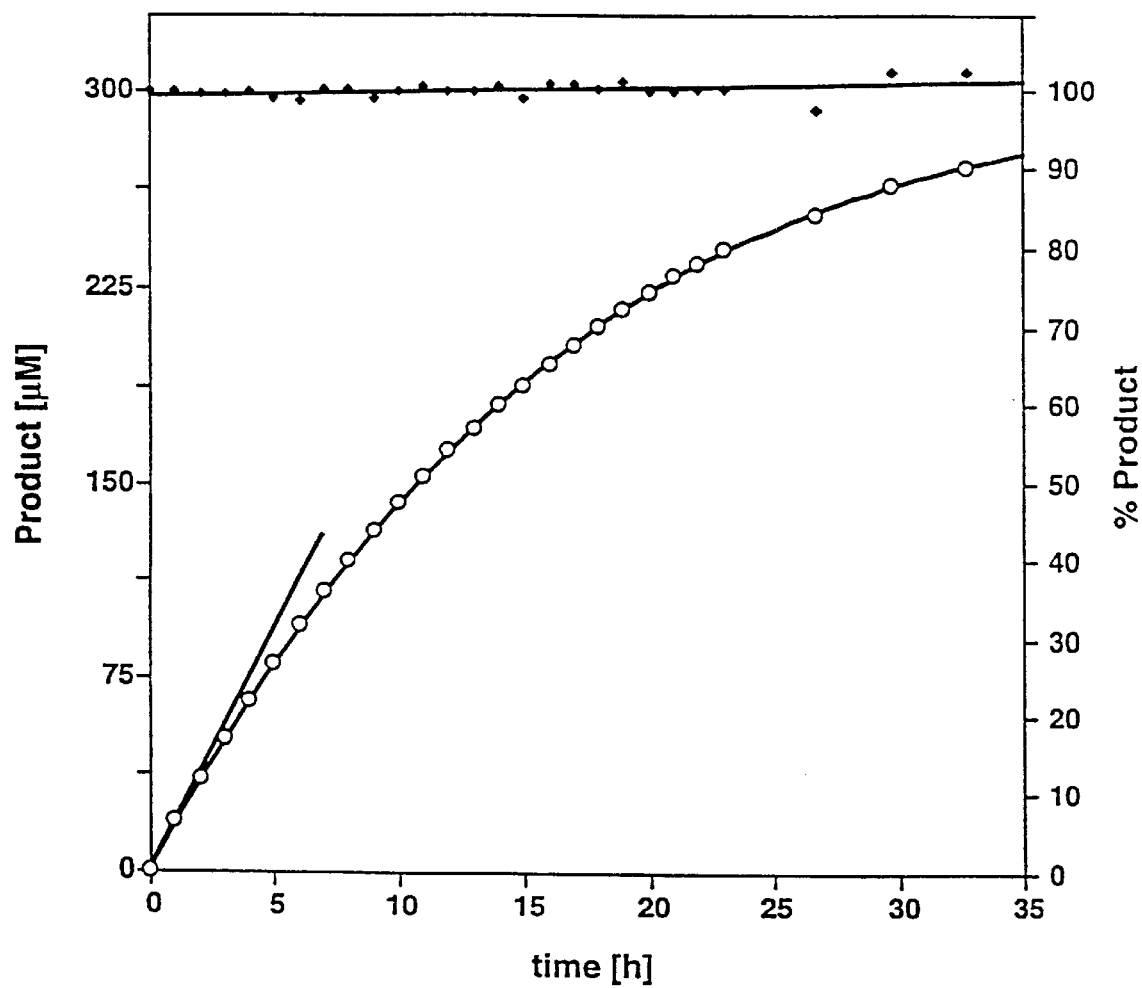

The reaction of the branched 3-phenylpropionaldehyde acceptor (6+7) (FIG. 9, entry 1) with acetone was the most efficient and showed little product inhibition (FIG. 8). In fact, less than 1 mole percent catalyst is sufficient to achieve high conversion of substrate in a relatively short time. The reaction produces only the desired aldol product as each mole of aldehyde consumed is converted to the β-hydroxy ketone product (9,10) (FIGS. 8 and 9). For this reaction, the rate of the uncatalyzed background reaction at pH=7.5 under identical conditions used in the antibody assays has been determined, $k_{uncat}=2.28\times10-7$ $M^{-1}min^{-1}$ (Reymond et al. Tetrahedron Lett. 36, 2575 (1995)). This allows for the efficiency of antibody mediated catalysis to be determined. For both antibodies, 38C2 and 33F12, $(k_{cat}/KM)/k_{uncat}$ is ~109. The efficiency of catalysis is due in a large part to an entropic advantage in the antibody catalyzed reaction which is reflected as a high effective molarity, kcat/kuncat >105 M. The catalytic efficiency (kcat/ KM) of antibody aldolases is only ~4000-fold slower than that of the most studied enzyme fructose-1,6-bisphosphate aldolase (Chang et al. Science 183, 1204 (1974); Tolan et al. Biochemistry 33, 12291 (1994)). The catalytic efficiency of antibody 38C2 for the reaction given in entry 1, FIG. 9 is 64-fold greater than that obtained with catalysis by the enzyme 2-deoxyribose-5-phosphate aldolase.

Product distribution of aldol products

Figure 7:
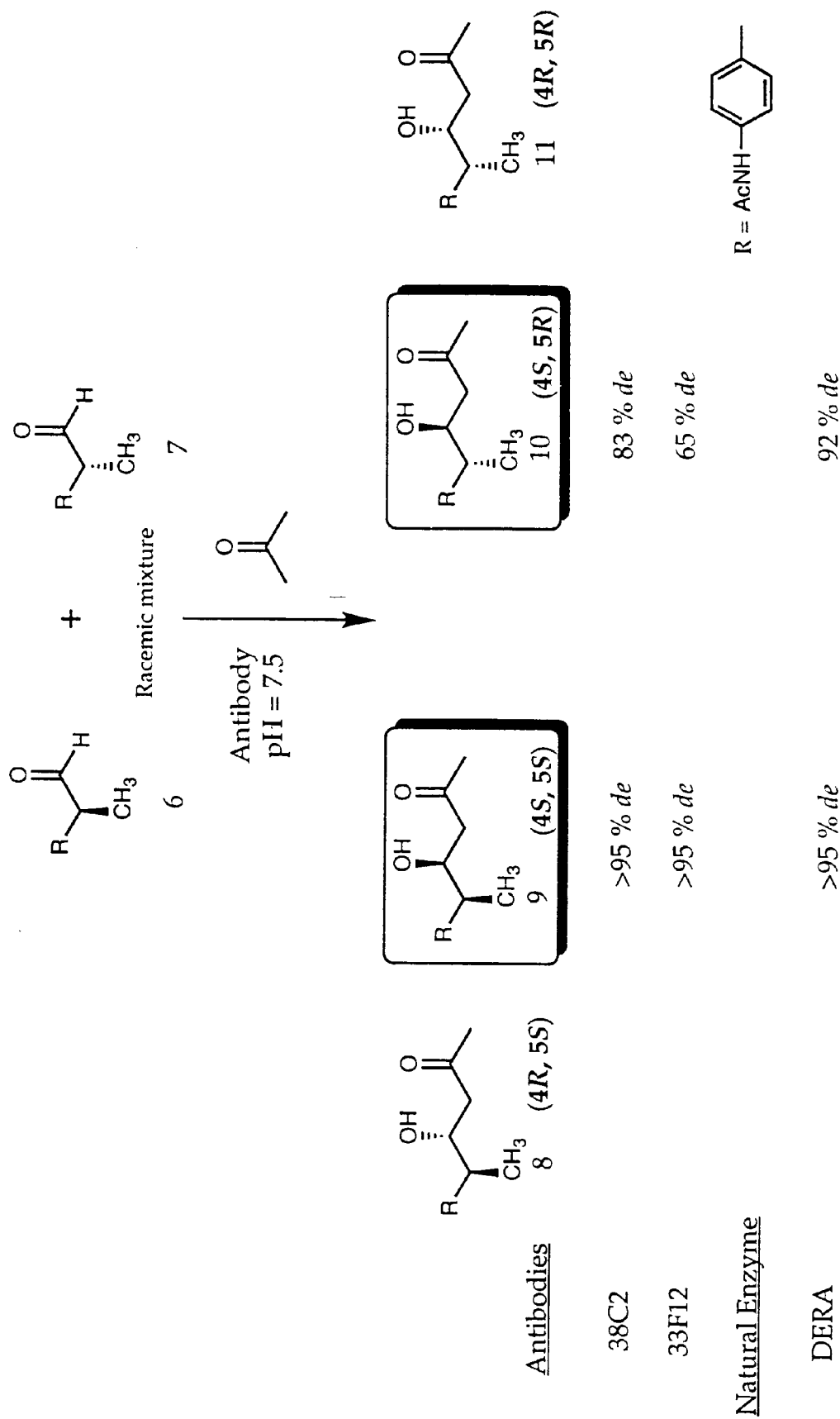
FIG. 7 illustrates the product distribution of the antibody-catalyzed reaction of (6+7) with aceton after 30% conversion with a normal-phase HPLC chiral support column.

The product distribution of the antibody catalyzed reaction of (6+7) with acetone was characterized. Product distribution was determined after 30% conversion with a normal-phase HPLC column of chiral support (FIG. 7). Both antibodies catalyze the diastereoselective addition of acetone to the re-face of (6+7) regardless of the stereochemistry at C-2 of this substrate. The four diastereoisomers have been separated on a DAICEL Chiralpak OJ column with an isocratic program 7/1; hexane/ethanol, 1 ml/min, 254 nm. The retention times for the four isomers were: 19.74 (4R, 5R), 23.32 (4R,5S), 25.15 (4S,5R), and 27.91 min (4S,5S). The relative configuration had been determined previously [A RP-C18 column (MICROSORB-MV, 0.45 cm by 22 cm) was used with an isocratic program of 77/23; H2O (0.1% trifluoroacetic acid)/H2O:acetonitrile 1:1, at 1.5 ml/min, monitored at 254 nm]. The retention times for the aldehyde (6+7) and the β-hydroxy ketone (13,14) are 19.20 and 21.92 min, respectively. The absolute configuration was deduced from an experiment wherein the catalyst was 2-deoxyribose-5-phosphate aldolase (DERA). DERA forms exclusively the aldol product possessing the (S) configuration at C-4 (C. -H. Wong and G. M. Whitesides, Enzymes in Synthetic Organic Chemistry (Permagon, Oxford, 1994). The aldol product generated by DERA consists of a 1:4.5 mixture of (4S,5R)-(compound 9) (92% diasteriomeric excess,de) and (4S,5S)-(compound 10) (>95% de). The kinetic parameters of this particuliar transformation were kcat=4.5×10–2 min–1 and Km=3400 mM. The aldol reactions follow the Cram-Felkin mode of attack on (S)-(6) to generate the (4S,5S)-9 product and the anti-Cram-Felkin mode of attack on (R)-(7) to generate the (4S,5R)-10 product. The antibodies formed these products with similar chemical yields, demonstrating no kinetic resolution of the racemic aldehyde in the aldol addition. The two antibodies distinguish themselves in their ability to control the diastereofacial selectivity of the reaction which reflects the ability of the catalysts to orient (6+7) in the binding pocket of the antibody relative to the nucleophilic antibody-enamine of acetone. This differential binding is also reflected in differences in KM for (6+7) in the antibodies (FIG. 9).

Figure 10:
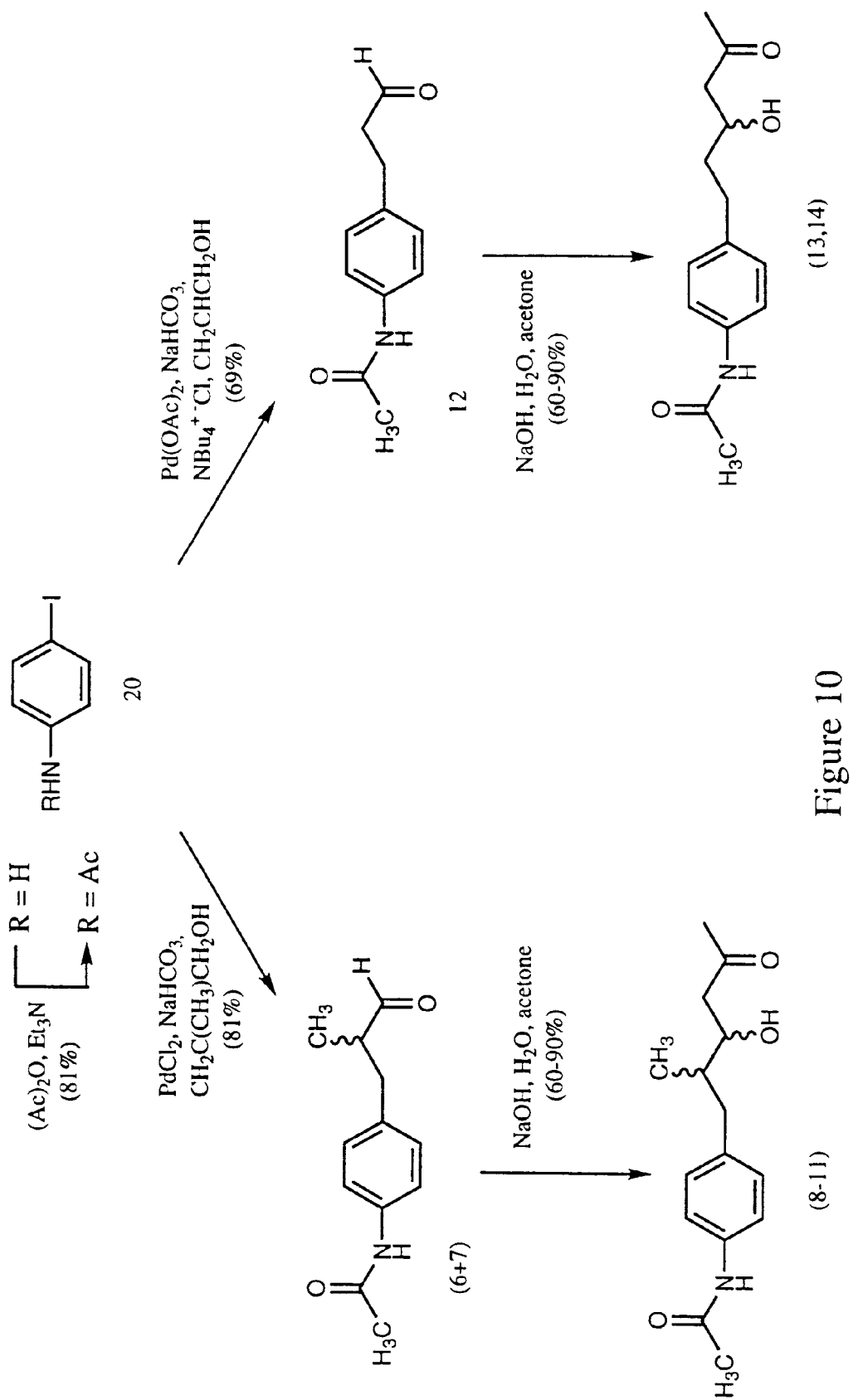
FIG. 10 illustrates the synthesis of aldehydes (6+7) and 12 from p-iodoaniline using the Heck reaction (Jeffrey et al. *J. Chem. Comm.* 1984, 1287). Product mixtures for the aldol addition were obtained from compounds (6+7) and 12 using NaOH, water and acetone.
Figure 11:
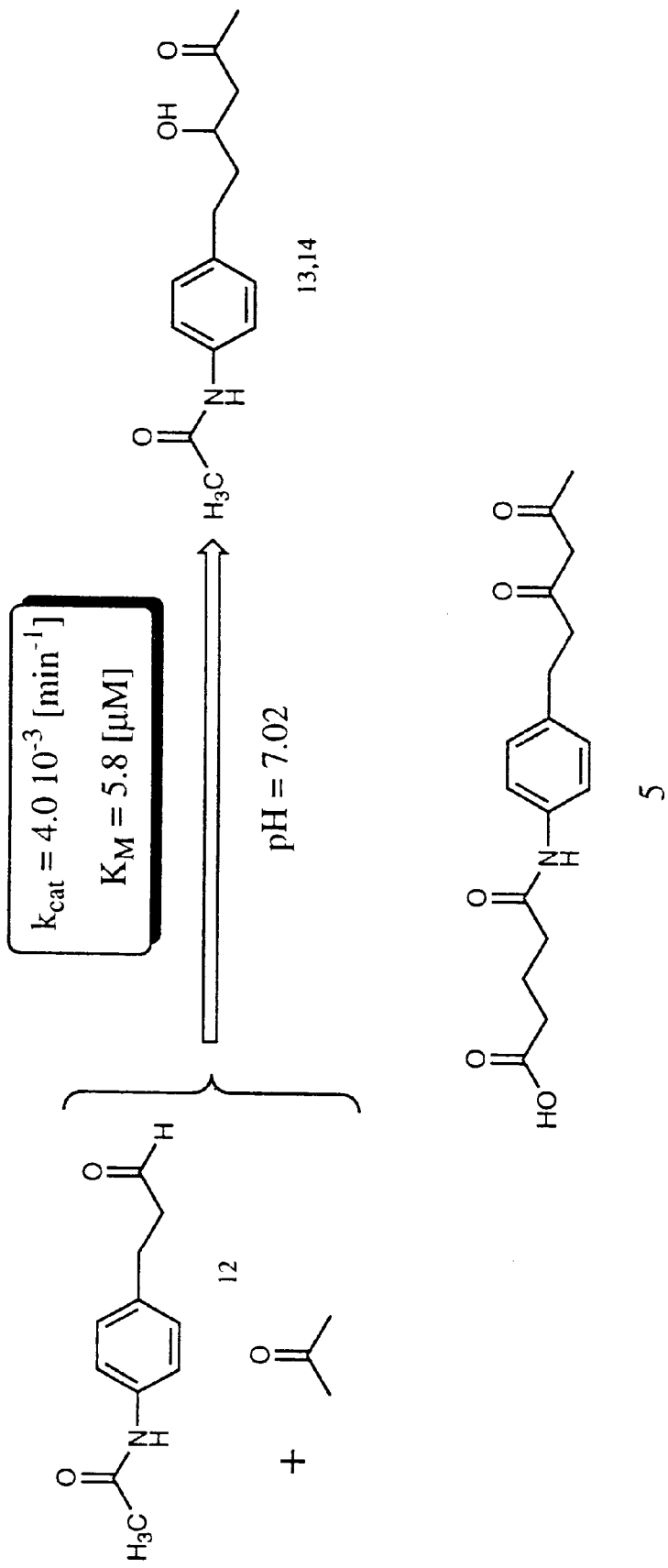
FIG. 11 illustrates the kinetics of the aldol reaction using antibody 38C2 and 33F12 derived from hapten 5, aldehyde 12 and acetone to afford compound 13/14 at pH=7.02. $K_{cat}=4.0 \cdot 10^{-3}$ [$min^{-1}$]; $K_M=5.8$ [$\mu M$].
Figure 12:
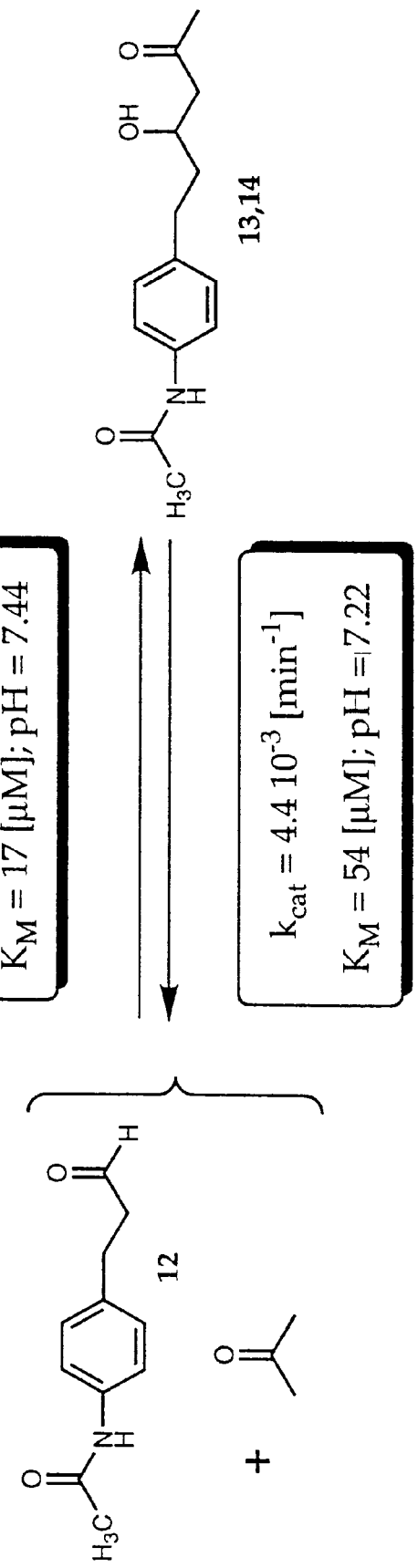
FIG. 12 illustrates aldol and retroaldol kinetics using antibody 38C2 and 33F12 derived from hapten 5, aldehyde 12 and acetone to afford compound 13/14. Forward arrow: Aldol reaction at pH=7.44: $K_{cat}=6.7 \cdot 10^{-3}$ [$min^{-1}$]; $K_M=17$ [$\mu M$]; Reverse Arrow: Retroaldol reaction at pH=7.22: $K_{cat}=4.4 \cdot 10^{-3}$ [$min^{-1}$]; $K_M=54$ [$\mu M$].

Synthesis of compound 20 (FIG. 10)

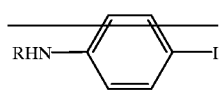

20

Compound 20: 1.0 equivalents of 4-iodoaniline (Aldrich) was suspended in 0.10 Molar methylene chloride and cooled to 0° C. Next, 1.1 equivalents acetic anhydride and 1.1 equivalnets triethylamine were added and the mixture was stirred for 2 hours at 0° C. Once the reaction was complete, as monitored by tlc, the mixture was quenched with successive saturated solution washes of ammonium chloride, water and dried over magnesium sulfate. The compound was evaporated and purified via flash column chromatography to afford compound 20 in 81% overall yield.

Synthesis of compounds (6+7) (FIG. 10)

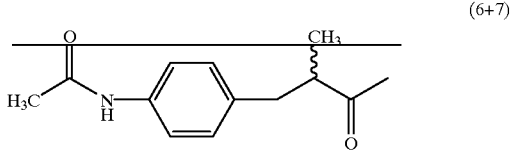

(6+7)

Compounds 6+7: Procedure using the Heck reaction as adapted from Jeffrey et al. J. Chem. Soc. Chem. Comm., 1287 (1984): 1.0 equivalents of compound 20 was suspended in 0.10 Molar dimethylformamide at 25–30° C. under nitrogen. Next, 1.1 equivalents sodium bicarbonate, 1.1 equivalents 2-methyl-2-propen-1-ol (Aldrich) and 2 mole % $PdCl_2$ were added and the mixture was stirred for 12 hours. Once the reaction was complete, as monitored by tlc, the mixture was diluted with ethylacetate and quenched with successive saturated solution washes of ammonium chloride, water and dried over magnesium sulfate. The compound was evaporated and purified via flash column chromatography to afford compounds 6+7 in 81% overall yield.

Synthesis of compounds (12) (FIG. 10)

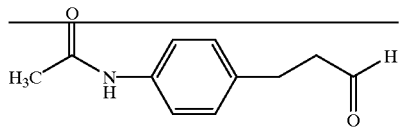

12

Compounds 12: Procedure using the Heck reaction as adapted from Jeffrey et al. *J. Chem. Soc. Chem. Comm.*, 1287 (1984): 1.0 equivalents of compound 20 was suspended in 0.10 Molar dimethylformamide at 25–30° C. under nitrogen. Next, 1.1 equivalents sodium bicarbonate, 1.1 equivalents allyl alcohol (Aldrich) and 2 mole % $PdCl_2$ were added and the mixture was stirred for 12 hours. Once the reaction was complete, as monitored by tlc, the mixture was diluted with ethylacetate and quenched with successive saturated solution washes of ammonium chloride, water and dried over magnesium sulfate. The compound was evaporated and purified via flash column chromatography to afford compounds 12 in 81% overall yield.

Synthesis of Compounds (8–11; 13,14—FIG. 10)

Typically, 50 to 100 mg aldehyde, 1 ml ketone, 4 ml $H_2O$ and 10 ml saturated NaOH sol. were shaken for 1 hour. The products were separated and purified by preparative reversed phase HPLC.

Characterization of Catalytic Specificity:

Although natural enzymes display broad specificity with respect to the aldol acceptor, the aldol donor is usually limited to the natural substrate. The most limiting aspect of the application of natural enzymes in synthesis is their rather poor acceptance of a range of substrates. In contrast, the donor substrate specificity of the aldolase antibodies disclosed herein is greatly enhanced as compared to natural enzymes. For example, among the ketones studied for antibody catalysis (FIG. 9) only acetone is a substrate for a natural enzyme. In contrast, antibody aldolases can use various aldol donors and acceptors. The antibodies accept acetone, fluoroacetone, chloroacetone, 2-butanone, 3-pentanone, 2-pentanone, and dihydroxyacetone, as aldol donor substrates. In reactions with 2-butanone and 2-pentanone the antibodies exhibit some control of the regioselectivity of the aldol addition by preferential formation of the most substituted enamine. The relative efficiency of catalysis with these substrates decreases 42-fold as reflected by kcat/KM in the acetone to pentanone series (FIG. 9). The failure of the antibodies to accept acetaldehyde as a donor demonstrates that the aldol addition is directed with a ketone as the aldol donor. In principle, the diketone hapten should induce antibodies that react at either of the two keto positions of the hapten 5, thereby generating catalysts which direct the aldol addition in either direction (FIG. 9). The two catalysts we have isolated are restricted in that they direct the aldol addition with acetone or aliphatic ketones as donors and 3-phenylpropionaldehyde derivatives as acceptors. Screening of additional antibodies should provide catalysts for the reaction wherein 3-phenylpropanone derivatives are accepted as aldol donors and aliphatic aldehydes serve as acceptors, as indicated in FIG. 9.

Deposit of Hybridomas:

Deposits for hybridoma 38C2 (JW 3862), having ATCC accession number HB 12005 and for hybridoma 33F12 (JW 33F12), having ATCC accession number HB 12004 were made in compliance with the Budapest Treaty requirements that the duration of the deposits should be for 30 years from the date of deposit at the depository or for the enforceable life of a U.S. patent that matures from this application, whichever is longer. The cell line will be replenished should it become non-viable at the depository.

What is claimed is:

1. A process for producing a first reaction intermediate having a Schiff base, the process comprising the following step:
   condensing a first reactant with a catalyst for producing said first reaction intermediate,
   wherein
      said catalyst having a catalytic amino group, said catalyst being selected from a group consisting of catalytic antibodies and catalytic molecules containing an antibody combining site portion characterized by having a lysine with an ε-amino group;
      said first reactant having a carbonyl group; and
      in said condensing step, the oxygen of the carbonyl group of said first reactant is displaced by the nitrogen of the catalytic amino group of said catalyst for forming said Schiff base, said Schiff base linking said first reactant to said catalyst for producing said first reaction intermediate.

2. A first reaction intermediate having a Schiff base produced by condensing a first reactant with a catalyst wherein:
   said catalyst having a catalytic amino group and being selected from a group consisting of catalytic antibodies and catalytic molecules containing an antibody combining site portion characterized by having a lysine with an ε-amino group;
   said first reactant having a carbonyl group, and
   in said condensing step, the oxygen of the carbonyl group of said first reactant is displaced by the nitrogen of the catalytic amino group of said catalyst for forming said Schiff base, said Schiff base linking said first reactant to said catalyst for producing said first reaction intermediate.

3. A process for producing a second reaction intermediate having a conjugated enamine, the process comprising the following step:
   tautomerizing a first reaction intermediate having a Schiff base for producing said second reaction intermediate having said conjugated enamine,
   wherein:
      said first reaction intermediate being described in claim 2; and
      in said tautomerization step, said Schiff base tautomerizes for forming said conjugated enamine and for producing said second reaction intermediate thereby.

4. A second reaction intermediate having a conjugated enamine produced by tautomerizing a first reaction intermediate, wherein:
   said first reaction intermediate being described in claim 2; and
   in said tautomerization step, said Schiff base tautomerizes for forming said conjugated enamine and for producing said second reaction intermediate thereby.

5. A process for producing a third reaction intermediate having a Schiff base, the process comprising the following step:

performing an addition reaction between a second reactant and a second reaction intermediate for producing said third reaction intermediate, wherein:
said second reactant having a carbonyl group;
said second reaction intermediate being described in claim 4; and
in said addition reaction, the α-carbon of said conjugated enamine of said second reaction intermediate is added to the carbon of the carbonyl group of said second reactant for linking said second reactant to said second reaction intermediate by means of a Schiff base and for producing said third reaction intermediate thereby.

6. A third reaction intermediate having a Schiff base produced by addition reaction between a second reactant and a second reaction intermediate, wherein:

said second reactant having a carbonyl group;
said second reaction intermediate being described in claim 4; and
in said addition reaction, the α-carbon of said conjugated enamine of said second reaction intermediate is added to the carbon of the carbonyl group of said second reactant for linking said second reactant to said second reaction intermediate by means of a Schiff base and for producing said third reaction intermediate thereby.

7. An adduct produced by condensing a β-dicarbonylic molecule with a catalyst having a catalytic amino group, the catalyst being selected from a group consisting of catalytic antibodies and catalytic molecules containing an antibody combining site portion characterized by having a lysine with an ε-amino group.

* * * * *